(12) United States Patent
Ferree

(10) Patent No.: US 6,719,797 B1
(45) Date of Patent: Apr. 13, 2004

(54) NUCLEUS AUGMENTATION WITH IN SITU FORMED HYDROGELS

(76) Inventor: Bret A. Ferree, 1238 Cliff Laine Dr., Cincinnati, OH (US) 45208

( * ) Notice: Subject to any disclaimer, the term of this patent is extended or adjusted under 35 U.S.C. 154(b) by 0 days.

(21) Appl. No.: 09/638,244

(22) Filed: Aug. 14, 2000

Related U.S. Application Data

(60) Provisional application No. 60/148,913, filed on Aug. 13, 1999.

(51) Int. Cl.[7] .................................................. A61F 2/44
(52) U.S. Cl. ...................... 623/17.16; 424/426; 623/908
(58) Field of Search ........................... 623/17.11–17.16, 623/11.11, 23.58, 23.59, 14.12; 424/78.17, 93.7, 426

(56) References Cited

U.S. PATENT DOCUMENTS

| | | | | |
|---|---|---|---|---|
| 5,047,055 A | * | 9/1991 | Bao et al. ................. | 623/17.11 |
| 5,192,326 A | * | 3/1993 | Bao et al. ................. | 623/17.11 |
| 5,318,780 A | | 6/1994 | Viegas et al. ............... | 424/427 |
| 5,376,693 A | | 12/1994 | Viegas et al. ............... | 523/106 |
| 5,587,175 A | | 12/1996 | Viegas et al. ............... | 424/427 |
| 5,709,854 A | * | 1/1998 | Griffith-Cima et al. .... | 424/93.7 |
| 5,718,862 A | | 2/1998 | Thompson .................. | 264/296 |
| 5,801,033 A | | 9/1998 | Hubbell et al. ............. | 435/182 |
| 6,129,761 A | * | 10/2000 | Hubbell ................... | 623/11.11 |
| 6,162,250 A | * | 12/2000 | Malice, Jr. et al. ............. | 623/7 |
| 6,187,048 B1 | * | 2/2001 | Milner et al. ............ | 623/17.12 |
| 6,214,331 B1 | * | 4/2001 | Vanderhoff et al. ...... | 424/78.17 |
| 6,231,605 B1 | * | 5/2001 | Ku .......................... | 623/11.11 |
| 6,231,615 B1 | * | 5/2001 | Preissman ................ | 623/23.73 |
| 6,352,557 B1 | * | 3/2002 | Ferree ..................... | 623/17.11 |
| 6,428,576 B1 | * | 8/2002 | Haldimann .............. | 623/17.16 |
| 6,443,988 B2 | * | 9/2002 | Felt et al. | |
| 6,605,294 B2 | * | 8/2003 | Sawhney .................... | 424/426 |

FOREIGN PATENT DOCUMENTS

WO    WO 98/20939    * 11/1997

OTHER PUBLICATIONS

Orthopedics Today, Jul. 2000.
"Proceedings 14th Annual Meeting"North American Spine Society, Oct. 1999.
"Proceedigns 13th Annual Meeting"North American Spine Society, Oct. 1998.

* cited by examiner

*Primary Examiner*—David H. Willse
*Assistant Examiner*—Suzette J. Jackson
(74) *Attorney, Agent, or Firm*—Gifford, Krass, Groh, Sprinkle, Anderson & Citkowski, PC

(57) ABSTRACT

Artificial disc augmentation for natural intervertebral discs using a solution of polymers. Once inserted into the disc the polymers crosslink to form hydrogels in vivo. Crosslinking of the polymers is activated by changes in temperature, pH, or ionic activity.

15 Claims, No Drawings

NUCLEUS AUGMENTATION WITH IN SITU FORMED HYDROGELS

REFERENCE TO RELATED APPLICATIONS

This application claims priority of U.S. provisional patent application Ser. No. 60/148,913, filed Aug. 13, 1999, the entire contents of which are incorporated herein by reference.

FIELD OF THE INVENTION

This invention relates generally to surgical techniques and prosthetic components therefor and, in particular, to intervertebral disc replacement apparatus and methods of implanting the same.

BACKGROUND OF THE INVENTION

Disc degeneration is thought to be the leading cause of chronic low back pain. Eighty-five percent of the population will experience low back pain at some point. Fortunately, the majority of people recover from their back pain with a combination of benign neglect, rest, exercise, medication, physical therapy, or chiropractic care. A small percent of the population will suffer chronic low back pain. The cost of treating patients with spinal disorders, plus the patient's lost productivity, is estimated at 25 to 100 billion dollars annually.

Seven cervical (neck), 12 thoracic, and 5 lumbar (low back) vertebra form the normal human spine. Intervertebral discs reside between adjacent vertebra with two exceptions. First, the articulation between the first two cervical vertebras does not contain a disc. Second, a disc lies between the last lumbar vertebra and the sacrum (a portion of the pelvis).

Motion between the vertebra occurs through the disc and two facet joints. The disc lies in the front or anterior portion of the spine. The facet joints lie laterally on either side of the posterior portion of the spine. The osseous—disc combination of the spine coupled with ligaments, tendons, and muscles are essential for spine function. The spine allows movement (flexion, extension, lateral bending, and rotation), supports the body, and protects the spinal cord and nerves.

The human intervertebral disc is an oval to kidney bean shaped structure of variable size depending on the location in the spine. Interestingly, the adult disc is the largest vascular structure in the human body. Most cells in the nucleus obtain their nutrition and fluid exchange through diffusion from small blood vessels in adjacent vertebra.

The outer portion of the disc is known as the annulus fibrosis. The annulus is formed of 10 to 60 fibrous bands. The fibers in the bands alternate their direction of orientation by 30 degrees between each band. The orientation serves to control vertebral motion (one half of the bands tighten to check motion when the vertebra above or below the disc are turned in either direction). The annulus contains the nucleus.

The nucleus pulpous serves to transmit and dampen axial loads. A high water content (70–80%) assists the nucleus in this function. The water content has a diurnal variation. The nucleus imbibes water while a person lies recumbent. Activity squeezes fluid from the disc. Nuclear material removed from the body and placed into water will imbibe water swelling to several times its normal size. The nucleus comprises 50% of the entire disc. The nucleus contains cells (chondrocyte like cells and fibrocytes) and proteoglycans (chondroitin sulfate and keratin sulfate). The cell density in the nucleus is 4,000 cells per micro liter.

The disc changes with aging. As a person ages the water content of the disc falls from approximately 85% at birth to 70% in the elderly. The ratio of chondroitin sulfate to keratin sulfate decrease with age. The ratio of chondroitin 6 sulfate to chondroitin 4 sulfate increases with age. The distinction between the annulus and the nucleus decreases with age. These changes are known as disc degeneration. Generally disc degeneration is painless.

Premature or accelerated disc degeneration is known as degenerative disc disease. As noted previously, a large portion of patients suffering from chronic low back pain are thought to have this condition. As the disc degenerates the nucleus and annulus functions are compromised. The nucleus becomes thinner and less able to handle compression loads. The annulus fibers become redundant as the nucleus shrinks. The redundant annular fibers are less effective in controlling vertebral motion. The disc pathology can result in: 1. Bulging of the annulus into the spinal cord or nerves. 2. Narrowing of the space between the vertebra where the nerves exit. 3. Tears of the annulus as abnormal loads are transmitted to the annulus and the annulus is subjected to excessive motion between vertebra. 4. Disc herniation or extrusion of the nucleus through complete annular tears.

Current surgical treatments of disc degeneration are destructive. One group of procedures removes the nucleus or a portion of the nucleus; lumbar discectomy falls in this category. A second group of procedures destroy nuclear material; Chymopapin (an enzyme) injection, laser discectomy, and thermal therapy (heat treatment to denature proteins) fall in this category. A third group, spinal fusion procedures either remove the disc or the disc's function by connecting two or more vertebra together with bone. These destructive procedures lead to acceleration of disc degeneration. The first two groups of procedures compromise the treated disc. Fusion procedures transmit additional stress to the adjacent discs. The additional stress results in premature disc degeneration of the adjacent discs.

Prosthetic disc replacement offers many advantages. The prosthetic disc attempts to eliminate a patient's pain while preserving the disc's function. Current prosthetic disc implants replace either the nucleus or the nucleus and the annulus. Both types of procedures remove the degenerated disc component to allow room for the prosthetic component.

Hydrogels have been used to replace the nucleus pulposis. The biomechanical properties of hydrogels closely replicate those of the nucleus pulposis. Like the nucleus, hydrogels have excellent visco-elastic properties, shape memory, and allow fluids to be imbibed and released from the hydrogel with cyclic loading.

Bao et. al., U.S. Pat. No. 5,192,326 and Ray et.al., U.S. Pat. No. 5,824,093 teach the use of hydrogels covered by constraining jackets or semi-permeable membranes. According to both patents, the encapsulated hyrogels are placed into the annulus fibrosis of the disc after removing the nucleus pulposis. Bao, et. al. (U.S. Pat. Nos. 5,047,066 and 5,800,549) also describe the use of non-encapsulated hydrogels. Both patents use hydrogels prepared in vitro. The in vitro formed hydrogels are either compressed or dehydrated to facilitate insertion into the disc. Similar to the disclosures of U.S. Pat. Nos. 5,192,326 and 5,824,093 the non-encapsulated hydrogels described in U.S. Pat. Nos. 5,047, 055 and 5,800,549 are placed into the disc after removing the nucleus pulposis. The contents of these references, as well as the teachings of U.S. Pat. Nos. 5,709,854; 6,060,053; and 5,587,175 are incorporated herein by reference.

SUMMARY OF THE INVENTION

This invention resides in artificial augmentation for natural intervertebral discs in humans and animals. In contrast to existing in vitro introduction techniques, the invention broadly prescribes injecting a gel into the annulus fibrosis for in situ formation. This allows substances according to the invention to be injected through the annulus fibrosis of the disc with or without removal of degenerated nucleus pulposis.

In the preferred embodiment, the compositions of the invention change from a relatively low-viscosity polymer solution to a higher viscosity, semisolid hydrogel following cross-linking. Various polymers are applicable to the invention, including polysaccharides, alkyl celluloses, hydroxyalkyl methyl celluloses, polyhosphazenes, hyaluronic acid, sodium chondroitin sulfate, polyacrylates, polycycanolacrylates, methyl methacrylate, 2-hydoxyethyl methacrylate, polyethylene oxide-polypropylene glycol block copolymers, cyclodextrin, polydextrose, dextran, gelatin, polygalacturonic acid, polyvinyl alcohol, polyvinyl pyrrolidone, polyvinyl acetate, polyalkylene glycols, polyethylene oxide, collagen, sulfonated polymers, vinyl ether monomers or polymers, alginate, polyvinyl amines, polyvinyl pyridine, and polyvinyl imidazole. Crosslinking may result from various phenomena, including a change in temperature, pH, ionic reaction, and combinations thereof.

The preferred gels have a final volume sized to consume at least a portion of the intervertebral disc space, and enable the body to cyclically compress and expand the gels in a manner similar to the disc material being aided. Initial volumes on the order of 1–8 cc are suitable, depending upon the condition/degeneration of the nucleus.

DETAILED DESCRIPTION OF THE INVENTION

As discussed in the Summary, this invention resides in intervertebral disc formation/augmentation based upon in situ gel formation. In contrast to existing in vitro introduction techniques, the invention allows appropriate substances to be injected through the annulus fibrosis of the disc with or without removal of degenerated nucleus pulposis. The initial, low-viscosity form of the liquid allows injection of the materials to form the gel into the disc utilizing current techniques such as a needle and syringe.

In the preferred embodiment, the compositions of the invention change from a relatively low-viscosity polymer solution to a higher viscosity, semisolid hydrogel following cross-linking. Various polymers are applicable to the invention, including polysaccharides, alkyl celluloses, hydroxyalkyl methyl celluloses, polyhosphazenes, hyaluronic acid, sodium chondroitin sulfate, polyacrylates, polycycanolacrylates, methyl methacrylate, 2-hydoxyethyl methacrylate, polyethylene oxide-polypropylene glycol block copolymers, cyclodextrin, polydextrose, dextran, gelatin, polygalacturonic acid, polyvinyl alcohol, polyvinyl pyrrolidone, polyvinyl acetate, polyalkylene glycols, polyethylene oxide, collagen, sulfonated polymers, vinyl ether monomers or polymers, alginate, polyvinyl amines, polyvinyl pyridine, and polyvinyl imidazole.

The preferred gels have a final volume sized to consume at least a portion of the intervertebral disc space, and enable the body to cyclically compress and expand the gels in a manner similar to the disc material being aided. Initial volumes on the order of 1–8 cc are suitable, depending upon the condition/degeneration of the nucleus.

In the preferred embodiment, the compositions of the invention change from a low viscosity liquid to a semisolid gel having a high viscosity resulting from cross-linking. The cross-linking occurs in situ based upon mammalian body temperature, pH, or reaction with naturally occurring substances such as calcium ions. As a further option, a polyion may be employed to enhance the crosslinking of the hydrogel.

I claim:

1. A method of treating disc disease, comprising the step of:
   injecting a polymer solution comprising a polymer into the disc being treated, the polymer being such that a crosslinked hydrogel forms in vivo subsequent to injection through a calcium ion reaction.

2. The method of claim 1, wherein the polymer is selected from the group consisting of polysaccharides, alkyl celluloses, hydroxyalkyl methyl celluloses, polyhosphazenes, hyaluronic acid, sodium chondroitin sulfate, polyacrylates, polycycanolacrylates, methyl methacrylate, 2-hydroxyethyl methacrylate, polyethylene oxide-polypropylene glycol block copolymers, cyclodextrin, polydextrose, dextran, gelatin, polygalacturonic acid, polyvinyl alcohol, polyvinyl pyrrolidone, polyvinyl acetate, polyalkylene glycols, polyethylene oxide, collagen, sulfonated polymers, vinyl ether monomers or polymers, alginate, polyvinyl amines, polyvinyl pyridine, and polyvinyl imidazole.

3. The method of claim 1, further including the step of using a polyion to enhance the crosslinking of the hydrogel.

4. The method of claim 1, wherein step of injecting the polymer solution into the disc being treated is carried out with a needle and syringe.

5. A method of augmenting an intervertebral disc having an annulus fibrosis, comprising the steps of:
   injecting a polymer solution comprising a polymer into the disc being treated, the solution exhibiting a sufficiently low viscosity permitting injection through the annulus fibrosis using a needle and syringe; and
   allowing the polymer to crosslink under an in situ mammalian condition to form a crosslinked hydrogel within the disc through a calcium ion reaction so as to form a higher-viscosity, semi-hard material enabling the body to cyclically compress and expand the disc in a manner similar to the disc material being augmented.

6. The method of claim 5, wherein the polymer is selected from the group consisting of polysaccharides, alkyl celluloses, hydroxyalkyl methyl celluloses, polyhosphazenes, hyaluronic acid, sodium chondroitin sulfate, polyacrylates, polycycanolacrylates, methyl methacrylate, 2-hydroxyethyl methacrylate, polyethylene oxide-polypropylene glycol block copolymers, cyclodextrin, polydextrose, dextran, gelatin, polygalacturonic acid, polyvinyl alcohol, polyvinyl pyrrolidone, polyvinyl acetate, polyalkylene glycols, polyethylene oxide, collagen, sulfonated polymers, vinyl ether monomers or polymers, alginate, polyvinyl amines, polyvinyl pyridine, and polyvinyl imidazole.

7. A method of treating disc disease, comprising the step of:
   injecting a polymer solution comprising a polymer into the disc being treated, the polymer being such that a crosslinked hydrogel forms in vivo subsequent to injection; and
   enhancing the crosslinking with a polyion.

8. The method of claim 7, wherein the crosslinked hydrogel is formed through temperature, pH, or ionic reaction.

9. The method of claim 8, wherein the ionic reaction is a calcium ion reaction.

10. The method of claim 7, wherein the polymer is selected from the group consisting of polysaccharides, alkyl celluloses, hydroxyalkyl methyl celluloses, polyhosphazenes, hyaluronic acid, sodium chondroitin sulfate, polyacrylates, polycycanolacrylates, methyl methacrylate, 2-hydroxyethyl methacrylate, polyethylene oxide-polypropylene glycol block copolymers, cyclodextrin, polydextrose, dextran, gelatin, polygalacturonic acid, polyvinyl alcohol, polyvinyl pyrrolidone, polyvinyl acetate, polyalkylene glycols, polyethylene oxide, collagen, sulfonated polymers, vinyl ether monomers or polymers, alginate, polyvinyl amines, polyvinyl pyridine, and polyvinyl imidazole.

11. The method of claim 7, wherein step of injecting the polymer solution into the disc being treated is carried out with a needle and syringe.

12. A method of augmenting an intervertebral disc having an annulus fibrosis, comprising the steps of:

injecting a polymer solution comprising a polymer into the disc being treated, the solution exhibiting a sufficiently low viscosity permitting injection through the annulus fibrosis using a needle and syringe; and allowing the polymer to crosslink under an in situ mammalian condition, using a polyion to enhance the crosslinking, to form a crosslinked hydrogel within the disc so as to form a higher-viscosity, semi-hard material enabling the body to cyclically compress and expand the disc in a manner similar to the disc material being augmented.

13. The method of claim 12, wherein the in situ mammalian condition allowing the solution to crosslink is temperature, or pH, or ionic reaction.

14. The method of claim 13, wherein the ionic reaction is a calcium ion reaction.

15. The method of claim 12, wherein the polymer is selected from the group consisting of polysaccharides, alkyl celluloses, hydroxyalkyl methyl celluloses, polyhosphazenes, hyaluronic acid, sodium chondroitin sulfate, polyacrylates, polycycanolacrylates, methyl methacrylate, 2-hydroxyethyl methacrylate, polyethylene oxide-polypropylene glycol block copolymers, cyclodextrin, polydextrose, dextran, gelatin, polygalacturonic acid, polyvinyl alcohol, polyvinyl pyrrolidone, polyvinyl acetate, polyalkylene glycols, polyethylene oxide, collagen, sulfonated polymers, vinyl ether monomers or polymers, alginate, polyvinyl amines, polyvinyl pyridine, and polyvinyl imidazole.

* * * * *